US007005557B2

(12) United States Patent
Klofta et al.

(10) Patent No.: US 7,005,557 B2
(45) Date of Patent: Feb. 28, 2006

(54) FILM-FORMING COMPOSITIONS FOR PROTECTING SKIN FROM BODY FLUIDS AND ARTICLES MADE THEREFROM

(75) Inventors: Thomas James Klofta, Cincinnati, OH (US); James Anthony Staudigel, Cincinnati, OH (US); George Endel Deckner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 614 days.

(21) Appl. No.: 09/898,880

(22) Filed: Jul. 3, 2001

(65) Prior Publication Data

US 2003/0077307 A1    Apr. 24, 2003

(51) Int. Cl.
*A61F 13/15*    (2006.01)
*A61F 13/20*    (2006.01)
(52) U.S. Cl. .............. 604/360; 424/400; 424/444; 428/98; 604/359; 604/367; 604/385.1
(58) Field of Classification Search ............. 424/400, 424/443, 444; 428/98; 604/359, 360, 367, 604/385.1
See application file for complete search history.

(56) References Cited

U.S. PATENT DOCUMENTS

| | | | |
|---|---|---|---|
| 2,804,424 A | 8/1957 | Stirn et al. | |
| 2,831,854 A | 4/1958 | Tucker et al. | |
| 3,464,413 A | 9/1969 | Goldfarb et al. | |
| 3,489,148 A | 1/1970 | Duncan et al. | |
| 3,490,454 A | 1/1970 | Goldfarb et al. | |
| 3,567,820 A | 3/1971 | Sperti | |
| 3,585,998 A | 6/1971 | Hayford | |
| 3,860,003 A | 1/1975 | Buell | |
| 3,875,942 A | 4/1975 | Roberts et al. | |
| 3,896,807 A | 7/1975 | Buchalter | |
| 3,902,493 A | 9/1975 | Baier et al. | |
| 3,920,015 A | 11/1975 | Wortham | |
| 3,935,862 A | 2/1976 | Kraskin | |
| 3,963,699 A | 6/1976 | Rizzi et al. | |
| 4,005,195 A | 1/1977 | Jandacek | |
| 4,005,196 A | 1/1977 | Jandacek et al. | |
| 4,034,077 A | 7/1977 | Hill et al. | |

(Continued)

FOREIGN PATENT DOCUMENTS

CA    2019557    6/1990

(Continued)

OTHER PUBLICATIONS

John A. Wenninger and G.N. McEwen, Jr., International Cosmetic Ingredient Dictionary and Handbook, 1997, THe Cosmetic, Toiletry, and Fragrance Association, vol. 1, pp. 26-27 and vol. 2, pp. 1067-1068.*

*Primary Examiner*—Sreeni Padmanabhan
*Assistant Examiner*—Konata M. George
(74) *Attorney, Agent, or Firm*—Eric T. Addington; Dara M. Kendall; Ken K. Patel

(57) ABSTRACT

The present invention relates to a film-forming barrier composition useful for protecting the skin from body fluids, such as urine, feces, menses. The composition comprises a skin conditioning agent, a viscosity enhancing agent and an oleophilic film-forming agent. Optionally, the lotion may comprise skin care ingredients for treating or maintaining skin health. The composition may be applied to the skin by suitable delivery vehicles, such as absorbent articles or components thereof, sheet materials, pads, bandages, sponges, foam pads, pumps, sprays, depending on the viscosity of the composition.

6 Claims, 1 Drawing Sheet

U.S. PATENT DOCUMENTS

| | | |
|---|---|---|
| 4,112,167 A | 9/1978 | Dake et al. |
| 4,138,416 A | 2/1979 | Koresawa et al. |
| 4,253,461 A | 3/1981 | Strickland et al. |
| 4,263,363 A | 4/1981 | Buck et al. |
| 4,324,247 A | 4/1982 | Aziz |
| 4,513,051 A | 4/1985 | Lavash |
| 4,517,360 A | 5/1985 | Volpenhein |
| 4,518,772 A | 5/1985 | Volpenhein |
| 4,556,146 A | 12/1985 | Swanson et al. |
| 4,556,560 A | 12/1985 | Buckingham |
| 4,569,343 A | 2/1986 | Kimura et al. |
| 4,589,876 A | 5/1986 | Van Tilburg |
| 4,597,760 A | 7/1986 | Buell |
| 4,597,761 A | 7/1986 | Buell |
| 4,623,339 A | 11/1986 | Ciraldo et al. |
| 4,666,765 A | 5/1987 | Caldwell et al. |
| 4,685,909 A | 8/1987 | Berg et al. |
| 4,687,478 A | 8/1987 | Van Tilburg |
| 4,704,112 A | 11/1987 | Suzuki et al. |
| 4,704,115 A | 11/1987 | Buell |
| 4,753,643 A | 6/1988 | Kassai |
| 4,790,836 A | 12/1988 | Brecher |
| 4,882,204 A | 11/1989 | Tenenbaum |
| 4,900,317 A | 2/1990 | Buell |
| 4,902,553 A | 2/1990 | Hwang et al. |
| 4,904,524 A | 2/1990 | Yoh |
| 4,909,802 A | 3/1990 | Ahr et al. |
| 4,940,464 A | 7/1990 | Van Gompel et al. |
| 4,950,264 A | 8/1990 | Osborn, III |
| 4,959,059 A | 9/1990 | Eilender et al. |
| 4,964,860 A | 10/1990 | Gipson et al. |
| 4,979,300 A | 12/1990 | Blank et al. |
| 4,990,144 A | 2/1991 | Blott |
| 4,996,238 A | 2/1991 | Matravers |
| 5,000,356 A | 3/1991 | Johnson et al. |
| 5,009,653 A | 4/1991 | Osborn, III |
| 5,043,155 A | 8/1991 | Puchalski et al. |
| 5,059,282 A | 10/1991 | Ampulski et al. |
| 5,091,193 A | 2/1992 | Enjolras et al. |
| 5,092,861 A | 3/1992 | Nomura et al. |
| 5,102,597 A | 4/1992 | Roe et al. |
| 5,151,092 A | 9/1992 | Buell et al. |
| 5,221,274 A | 6/1993 | Buell et al. |
| 5,246,433 A | 9/1993 | Hasse et al. |
| 5,264,460 A | 11/1993 | Jakobson et al. |
| 5,267,992 A | 12/1993 | Van Tilburg |
| 5,304,161 A | 4/1994 | Noel et al. |
| 5,306,514 A | 4/1994 | Letton et al. |
| 5,306,515 A | 4/1994 | Letton et al. |
| 5,306,516 A | 4/1994 | Letton et al. |
| 5,321,098 A | 6/1994 | Lal |
| 5,370,132 A | 12/1994 | Weber et al. |
| 5,376,655 A | 12/1994 | Imaki et al. |
| 5,389,094 A | 2/1995 | Lavash et al. |
| 5,409,903 A | 4/1995 | Polak et al. |
| 5,413,568 A | 5/1995 | Roach et al. |
| 5,415,649 A | 5/1995 | Watanabe et al. |
| 5,429,816 A | 7/1995 | Hofrichter et al. |
| 5,436,007 A | 7/1995 | Hartung et al. |
| 5,460,623 A | 10/1995 | Emenaker et al. |
| 5,489,283 A | 2/1996 | Van Tilburg |
| 5,509,915 A | 4/1996 | Hanson et al. |
| 5,525,345 A | 6/1996 | Warner et al. |
| 5,525,346 A | 6/1996 | Hartung et al. |
| 5,552,136 A | 9/1996 | Motley |
| 5,554,145 A | 9/1996 | Roe et al. |
| 5,558,655 A | 9/1996 | Jezzi et al. |
| 5,569,231 A | 10/1996 | Emenaker et al. |
| 5,569,234 A | 10/1996 | Buell et al. |
| 5,580,411 A | 12/1996 | Nease et al. |
| 5,607,760 A | 3/1997 | Roe |
| 5,609,587 A * | 3/1997 | Roe .......................... 604/360 |
| 5,620,430 A | 4/1997 | Bamber |
| 5,635,191 A | 6/1997 | Roe et al. |
| 5,643,588 A | 7/1997 | Roe et al. |
| 5,871,763 A | 2/1999 | Luu et al. |
| 5,938,649 A | 8/1999 | Ducker et al. |
| 6,043,168 A | 3/2000 | Colman et al. |
| 6,066,673 A | 5/2000 | McIver et al. |
| 6,107,537 A | 8/2000 | Elder et al. |
| 6,118,041 A * | 9/2000 | Roe et al. ................... 604/360 |
| 6,120,487 A | 9/2000 | Ashton |
| 6,120,488 A | 9/2000 | VanRijswijck et al. |
| 6,120,489 A | 9/2000 | Johnson et al. |
| 6,120,783 A | 9/2000 | Roe et al. |
| 6,149,934 A | 11/2000 | Krzysik et al. |
| 6,153,209 A | 11/2000 | Vega et al. |
| 6,156,024 A | 12/2000 | Schulte et al. |
| 6,166,285 A | 12/2000 | Schulte et al. |
| 6,204,208 B1 | 3/2001 | Krzysik et al. |
| 6,217,890 B1 | 4/2001 | Paul et al. |
| 6,228,385 B1 | 5/2001 | Shick |
| 6,287,581 B1 | 9/2001 | Krzysik et al. |

FOREIGN PATENT DOCUMENTS

| | | |
|---|---|---|
| DE | 4136540 A1 | 11/1991 |
| EP | 0 297 828 A1 | 1/1989 |
| EP | 0 631 768 A1 | 1/1995 |
| EP | 0 692 263 B1 | 1/1996 |
| EP | 0 922 452 A1 | 6/1999 |
| EP | 0 922 456 A1 | 6/1999 |
| GB | 2 033 751 A | 5/1980 |
| JP | 61-028078 | 2/1986 |
| JP | HEI 2(1990)31756 | 2/1990 |
| JP | 05-285170 | 11/1993 |
| JP | 8-52175 | 2/1996 |
| WO | WO 99/45973 | 9/1999 |
| WO | WO 99/45974 | 9/1999 |
| WO | WO 99/45976 A1 | 9/1999 |
| WO | WO 00/10500 A1 | 3/2000 |
| WO | WO 00/69484 A1 | 11/2000 |
| WO | WO 01/00156 A1 | 1/2001 |
| WO | WO 01/00157 A1 | 1/2001 |
| WO | WO 01/43717 A1 | 6/2001 |
| WO | WO 01/48312 A1 | 7/2001 |
| WO | WO 01/83876 A1 | 11/2001 |
| WO | WO 01/85128 A2 | 11/2001 |

* cited by examiner

FILM-FORMING COMPOSITIONS FOR PROTECTING SKIN FROM BODY FLUIDS AND ARTICLES MADE THEREFROM

FIELD OF THE INVENTION

The present invention relates to film forming compositions that provide a protective barrier against fluids, body exudates and other irritants, and minimize abrasions between skin and articles worn adjacent to the skin. The present composition form a thin film coating over the skin which is resistant to wash-off by water or body fluids and resistant to rub-off by abrasions. Thus, the persistent coating formed by the present composition provides an efficient delivery of skin care ingredients to skin and long-lasting skin condition and skin health benefits. The present invention also relates to articles having the film-forming compositions disposed thereon.

BACKGROUND OF THE INVENTION

The major function of disposable absorbent products, such as diapers, training pants, incontinence articles, sanitary napkins, panty liners, and the like, is to absorb and contain body exudates. Although these absorbent articles may be highly efficient for the absorption of liquids, they may also create a humid micro-environment adjacent to the body regions where they are worn. This humid micro-environment often results in overhydration of the skin. It is known that overhydrated skin is more susceptible to skin disorders, including erythema (i.e., redness), diaper rash or diaper dermatitis, heat rash, and skin barrier break-down, and skin damages relating to abrasions and pressure marks.

It is well recognized that compositions for treating diapered skin should desirably have barrier protective qualities. Additionally, the compositions should desirably have good affinity to the skin and are resistant to rub-off or wash-off such that they provide long-lasting barrier protection to the skin. Many compositions contain an emulsion type carrier that has a water phase and an oil phase. The relative high water content of the emulsion type compositions tends to exacerbate the overhydration problem of the diapered skin. Other compositions contain high contents of volatile carriers, such as low molecular weight silicones, alcohols or other solvents, which evaporate and leave a substantive residue on the skin. However, vapors from these volatile carriers may irritate the skin of certain individuals. Other compositions contain an anhydrous substantive carrier, such as petrolatum or organic waxes. These compositions have a greasy and tacky feel when applied to the skin, and tend to transfer onto and stain clothing or other surfaces which contact the area of application.

Therefore, it is desirable to provide a composition that has good affinity to the skin such that it resists rub-off by abrasion with clothing or other contacting surfaces, and wash-off by water or body liquids such as urine, menses, sweat, and runny bowl movement (BM).

It is further desirable to provide a composition that forms a film, which adheres to the skin and contains beneficial skin care ingredients that are held in intimate contact with the skin by the film forming nature of the composition.

It is also desirable to provide a composition that is substantive and forms a protective barrier on the skin. Such barrier protects the skin from direct contact with moisture, body exudates or other irritants. Such barrier also minimizes abrasions between the skin and clothing or other contacting surfaces.

It is further desirable that this novel composition may be administered to the target skin area via multiple delivery vehicles, such as pads, bandages, patches, sticks, aerosol dispensers, pump sprays, trigger sprays, canisters, and disposable absorbent articles. In this respect, it is desirable that the composition may be administered to the target skin without leaving a messy aesthetically unpleasing residue on the skin. It is further desirable that the composition may be administered without direct contact with the users' or applicators' hands, thus, no messy residue is left on the user's hands and no additional cleaning step is required after administering the composition.

Moreover, it is desirable that this novel composition is solid or semi-solid at ambient temperature so that it is immobilized on the surface of or within the cavity of the delivery vehicle. This is especially desirable when the delivery vehicle is an absorbent article. The immobilization of the composition minimizes the migration of the composition into the absorbent article, which interferes with the absorbency of the article and renders less composition available for delivery to the skin. The composition should preferably soften, plasticize or become flowable at or near skin temperature, or when a slight pressure or shear force is applied, so that it is readily transferable to the skin.

SUMMARY OF THE INVENTION

The present invention relates to a substantially anhydrous, film-forming composition that forms a protective barrier on the skin. Specifically, the composition of the present invention comprises:
  a. from about 1% to about 90% a skin conditioning agent;
  b. from about 15% to about 50% a viscosity enhancing agent;
  c. from about 1% to about 20% an oleophilic film-forming agent; and
  d. optionally, from about 0.01% to about 15% of a skin care ingredient.

The composition may be applied to the skin by suitable delivery vehicles, such as absorbent articles or components thereof, sheet materials, wipes, pads, bandages, sponges, foam pads, pumps, sprays, and combinations thereof.

DETAILED DESCRIPTION OF THE INVENTION

I. Definitions

Figure 1:
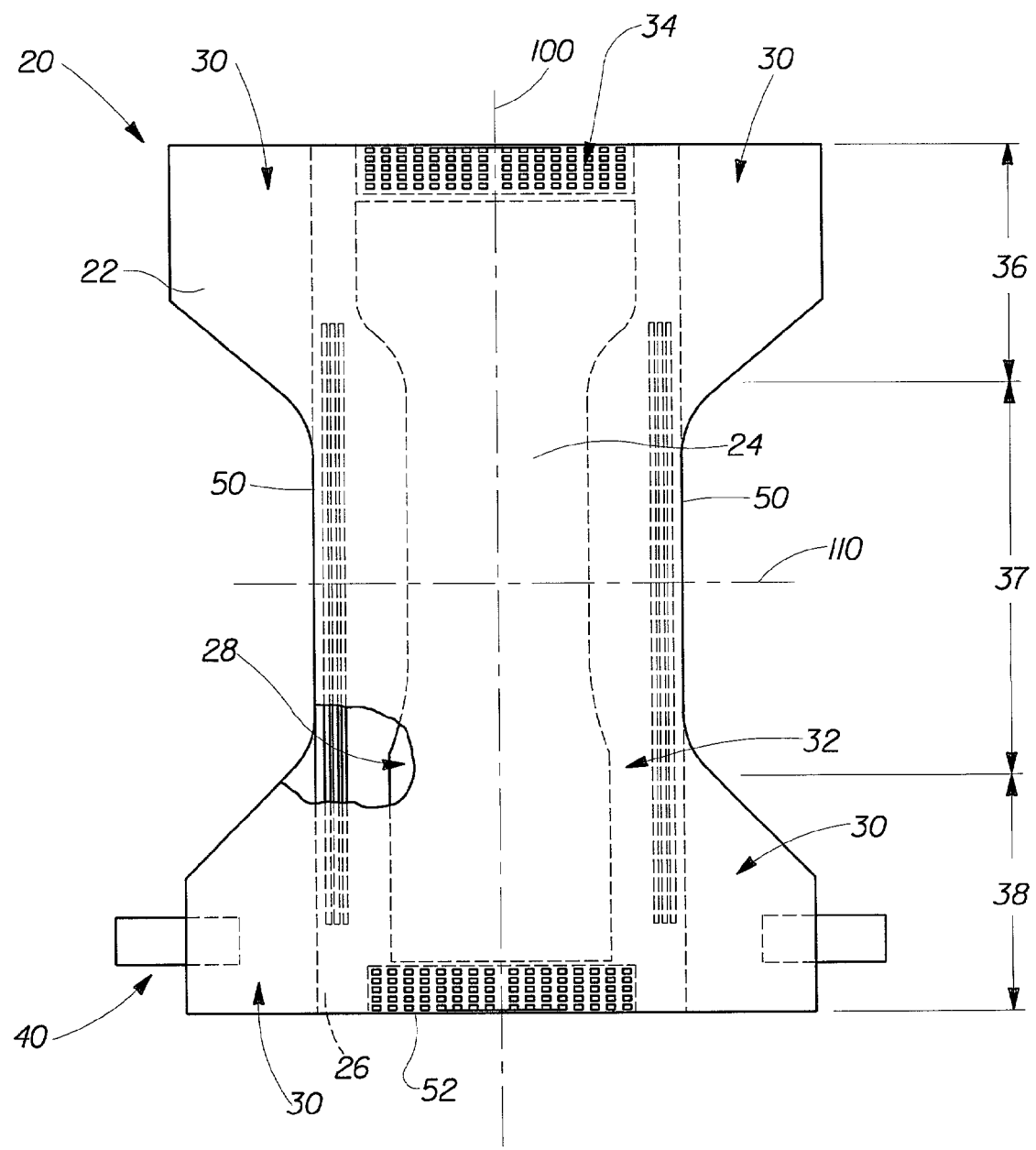
FIG. 1 shows an absorbent article in the form of a diaper suitable for use in the present invention.

As used herein, the term "comprising" means that the various components, ingredients, or steps can be conjointly employed in practicing the present invention. Accordingly, the term "comprising" encompasses the more restrictive terms "consisting of" and "consisting essentially of".

As used herein, the term "absorbent article" refers to a device which absorbs and retains body fluids. Examples of disposable absorbent articles include diapers, training pants, pull-on diapers, feminine hygiene garments, such as sanitary napkins, panti-liners, interlabial devices and tampons, incontinence articles, and the like.

As used herein, the term "disposable" refers to absorbent articles which generally are not intended to be laundered or otherwise restored or reused as absorbent articles (i.e., they are intended to be discarded after a single use).

As used herein, the term "skin care ingredient" means a substance or a mixture of substances, when applied to the skin, either alone or incorporated into a composition, provides barrier protections, skin healing benefits and/or skin conditioning benefits, such as actual or perceived changes in appearance, skin feel (e.g., softness, smoothness), cleanliness and attractiveness. The term is also directed to substances that soothe, calm, or promote feelings of relief when applied to the skin. These soothing, calming ingredients may include herbal, botanical, vitamin, mineral or aromatic ingredients. The term further includes substances that protect skin against moisture or irritants, and heals skin disorders or damages.

Other terms are defined herein where initially discussed.

All percentages, ratios and proportions used herein are defined by weight of the composition unless otherwise specified.

II. The Film-Forming Composition

The composition of the present invention comprises a skin conditioning agent, a viscosity enhancing agent and an oleophilic film-forming agent. Optionally, the composition may comprise skin care ingredients for treating or maintaining skin health. When the composition is applied to the skin, a relatively uniform film is formed on the skin surface. The barrier nature of the present composition protects the skin from direct contact with body exudates, including liquids or irritants therein. The film forming nature of the present composition provides good affinity to the skin such that the composition is resistant to wash-off or rub-off. Additionally, the film formed on the skin surface holds the skin care ingredients in intimate contact. Thus, the present composition provides an efficient and extended delivery of the relatively expensive skin care ingredients to the skin.

Further, the compositions used in the present invention are preferably substantially anhydrous, especially if the delivery vehicle is an absorbent article. As used herein, the term "substantially anhydrous" means the composition typically has a water content of less than about 10%, preferably less than about 5%, more preferably less than about 1%, and most preferably less than about 0.5% by weight. The substantially anhydrous nature of the compositions avoid the overhydration problem of the already susceptible skin that has been or is exposed to a high relative humidity microenvironment. Furthermore, such compositions minimize the potential wicking effect of the highly absorbent core, which preferentially draws compositions containing ample water towards the core, thus, reduces the amount of compositions available for transfer to the skin. If drawn into the core, the oleaginous composition of the present invention may interfere with the absorbency of the core.

In a preferred embodiment, the composition is applied to the skin using an absorbent article as the delivery vehicle. Suitable compositions for such delivery vehicles should have a melting/rheological profile that meets certain requirements. The compositions should preferably be solid or semi-solid at room temperature (i.e., about 20° C.) so that "migration" on the substrate surface and the adverse effects to the absorbency of the article are minimized. The compositions should also be at least partially transferable to the skin by contact, normal wear motions and/or body heat; therefore, the compositions are preferably plastic or fluid at skin temperature (i.e., about 34–36° C.) to facilitate the transfer to the skin. Further, the compositions should have storage stability under "stressful" storage conditions, such as storage temperatures of at least about 45° C. Since the compositions are substantially immobilized and stable in storage, special barrier or wrapping materials may be unnecessary in packaging the treated absorbent articles useful in the present invention.

The term "semisolid", as used herein, means that the composition has a rheology typical of pseudoplastic or plastic liquids. When no shear is applied, the compositions can have the appearance of a semi-solid but can be made to flow as the shear rate is increased. Without intending to be bound by theory, it is believed that while such compositions contain primarily solid components, they also include some liquid components.

To enhance the immobility of the preferred compositions, the viscosity of the formulated compositions should be as high as necessary to prevent substantial flow within the article to undesired locations. Specifically, the compositions of the present invention have a zero shear viscosity at room temperature between about $1.0 \times 10^6$ centipoise and about $1.0 \times 10^8$ centipoise. More preferably, the zero shear viscosity is between about $5.0 \times 10^6$ centipoise and about $5.0 \times 10^7$ centipoise.

On the other hand, too high a viscosity may inhibit transfer of the composition to the skin. Therefore, a balance should be achieved so the viscosities are high enough to keep the compositions localized on the surface of the article, but not so high as to impede transfer to the skin. In addition, the compositions preferably have a final melting point above skin temperature, more preferably above potential "stressful" storage conditions that can be greater than 45° C. (e.g., warehouse in Arizona, car trunk in Florida, etc.). Therefore, the preferred compositions will have the following melt profile:

| Characteristic | Preferred Range | Most Preferred |
|---|---|---|
| % liquid* at room temp. (20° C.) | 1–50 | 2–25 |
| % liquid* at skin temp. (34–36° C.) | 15–95 | 20–90 |
| final melting point (° C.) | ≧38 | ≧45 |

A. Skin Conditioning Agents

As used herein, the term "skin conditioning agent" means a material that protects against wetness or irritation, softens, soothes, supples, coats, lubricates, reduces flaking, moisturizes, protects and/or cleanses the skin. Skin conditioning agents may maintain the normal, healthy skin condition. One type of skin conditioning agents, generally referred to as emollients, are particularly useful in improving the dry skin condition by restoring its moisture level as well as its softness, smoothness, pliability, and flexibility. Another type of skin conditioning agents, generally referred to as moisturizers or humectants, attract moisture from the surrounding atmosphere and enhance the water absorption of the stratum corneum (i.e., the outer, corny layer of the skin). Another type of skin conditioning agents, generally referred to as barrier protectants, which form an occlusive (i.e., non-water-permeable) layer on the skin surface that prevents or retards moisture losses from the deeper layers of the skin to the atmosphere. The occlusive agents also provide barrier protection to the skin against larger molecules, such as fecal matter, urine, enzymes, and other irritants.

The amount of skin conditioning agent included in the composition will depend on a variety of factors, including the particular skin conditioning agent involved, the skin benefits desired, the other components in the composition, and like factors. The skin conditioning agents will generally comprise from about 1 to about 90 wt % of the composition. Preferably, the skin conditioning agents comprise from about 10 to about 85 wt %, more preferably from about 20 to about 80 wt %, and most preferably from about 30 to about 75 wt %, of the composition.

Exemplary skin conditioning agents useful in the present invention include, but are not limited to, petroleum-based emollients; fatty acid esters; polysiloxanes; polyol polyesters; esters or ethers of polyhydroxy alcohols; fatty alcohol esters of polyprotonic acids; animal oils, fats, and their derivatives; vegetable oils, hydrogenated vegetable oils, and their derivatives; branched hydrocarbons; fatty alcohol ethers; free sterols, sterol esters and their derivatives; sphingolipids; phospholipids; and mixtures thereof.

Suitable petroleum-based emollient include petrolatums, i.e., hydrocarbons or mixtures of hydrocarbons; particularly preferred are hydrocarbons having chain lengths of from C10 to C100. Petroleum-based emollients within this chain length range include mineral oil and petrolatum. Mineral oil usually refers to less viscous mixtures of hydrocarbons having from 10 to 30 carbon atoms, though the hydrocarbon molecular weight distribution may vary. Since the lower molecular weight hydrocarbons can cause irritation in some individuals, mineral oils having a small percentage of lower molecular weight hydrocarbons are preferred. Petrolatum usually refers to more viscous mixtures of hydrocarbons of higher molecular weight hydrocarbons. Petrolatum and mineral oil are preferred skin conditioning agents for compositions of the present invention due to their ability to protect the skin from harmful or irritating stimuli. Petrolatum is particularly preferred because of its good barrier properties. When employed, petrolatum comprises at least about 15 wt %, preferably at least about 25 wt %, more preferably at least about 50 wt % of the composition.

Suitable fatty acid ester type skin conditioning agents include those derived from $C_{12}$–$C_{50}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester skin conditioning agents can also be derived from esters of long chain fatty alcohols ($C_{12}$–$C_{50}$, preferably $C_{12}$–$C_{22}$) and short chain acids (e.g., lactic acid), such as lauryl lactate and cetyl lactate. Also suitable for use herein are fatty acid esters having branched and/or unsaturated alkyl chains in their acid or alcohol moieties. Nonlimiting examples include diisopropyl adipate (available as CERAPHYL® 230 from International Specialty Products, Wayne, N.J.), octyldodecyl stearoyl stearate, isononyl isononanoate (available as SALACOS® 99 from Ikeda Corp., Island Park, N.Y.), isostearyl isononanoate, octyl palmitate, octyl hydroxystearate, stearyl heptanoate, ceterayl octanoate, butyl octanol, 2-ethylhexyl-12-hydroxy stearate, decyl oleate, dioctyl adipate, dioctyl succinate, isocetyl stearate, octyl cocoate, octyl palmitate, and mixtures thereof. Other suitable fatty acid esters include laurel laureate, stearyl palmitate and stearyl behenate (available as PURESTER® 24, 34, and 40 from Strahl & Pitsch, West Babylon, N.Y.). Suitable fatty acid esters also include certain branched esters, such as cetearyl octanoate (CRODAMOL® CAP), lignoceryl erucate (CRODAMOL® LGE), and pentaerythrityl tetracaprylate/tetracaprate (CRODAMOL® PTC); all are available from Croda Inc., Parsippany, N.J.

Other suitable skin conditioning agents are polyol polyesters, including the "liquid" polyol polyesters which have a complete melting temperature at or below body temperature (i.e., about 37° C.) and the "solid" polyol polyesters which are solid or semi-solid at or above body temperature. As used herein, the term "polyol" means a polyhydric alcohol containing at least 2, preferably from 4 to 12, and most preferably from 6 to 8 hydroxy groups. Polyols include mono- di- and tri-saccharides, sugars, sugar alcohols, other sugar derivatives (e.g., alkyl glucosides), pentaerythritol and polyvinyl alcohol. Exemplary polyols include, but are not limited to, polyhydric alcohols such as pentaerythritol; sugars such as raffinose, maltodextrose, galactose, sucrose, glucose, xylose, fructose, maltose, lactose, mannose and erythrose; and sugar alcohols such as erythritol, xylitol, malitol, mannitol and sorbitol. Such polyols are esterified with fatty acids and/or other organic radicals having at least 2 carbon atoms and up to 30 carbon atoms. While it is not necessary that all of the hydroxyl groups of the polyol be esterified, the preferred polyol polyesters have substantially all (e.g., at least about 85%) of the hydroxyl groups esterified. Particularly preferred are sucrose polyol polyesters such as sucrose polycottonate, sucrose polysoyate, and sucrose polybehenate. Mixtures of such polyol polyesters are also suitable skin conditioning agents for the present invention. Other suitable polyol polyesters and mixtures thereof are disclosed in U.S. Pat. No. 5,609,587, issued to Roe on Mar. 11, 1997, and in U.S. Pat. No. 5,607,760, issued to Roe on Mar. 4, 1997, the disclosure of each is incorporated herein by reference. Other ester materials are further described in U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein.

Also useful herein are esters of polyhydroxy alcohols, which are generally used as the humectant-type skin conditioning agents. This type of esters may include glyceryl esters including glycerides and derivatized glycerides, polyglyceryl esters, and glycolic esters. Glyceryl esters are derived from glycerin, its derivatives and one or more carboxylic acid moieties. Non-limiting examples include various C1–C30 mono-, di- or tri-esters of glycerin and derivatives thereof, such as mono-, di-, tri-glycerides, acetoglycerides, and ethoxylated glycerides. Exemplary glyceryl esters include glyceryl behenate, glyceryl oleate, glyceryl stearate, glyceryl palmitate, glyceryl distearate, glyceryl dipalmitate, and the like. Polyglyceryl esters having C12–C22 acid moieties are also suitable for use herein. Non-limiting examples include polyglyceryl-4 isostearate, polyglyceryl-3 oleate, diglyceryl monooleate, tetraglyceryl monooleate and the like. Glycolic esters are derived from C2–C6 glycols, including ethylene glycol, propylene glycol, butylene glycol, hexylene glycol and derivatives thereof, and one or more carboxylic acid moieties having C1–C30 chains. Specific examples of glycolic esters include polyethylene glycols (PEGs), such as PEG-2, PEG-3, PEG-30 and PEG-50, and polypropylene glycols (PPGs), such as PPG-9, PPG-12, PPG-15, PPG-17, PPG-20, PPG-26, PPG-30 and PPG-34.

Also useful herein are fatty alcohol esters of polyprotonic acids, including mon-, di- or tri-esters derived from C8–C30 fatty alcohols and citric acid, malic acid, adipic acid, sebacic acid and the like.

Ethers of polyhydroxy alcohols, such as dialkyl ethers having C12–C30 alkyl chains or alkyl ethers having one C12–C30 alkyl chain and a lower (C1–C8) alkyl chain, are also suitable skin conditioning agents for the present invention. Glycolic ethers, such as C4–C20 alkyether of PEG or PPG, di-C8–C30 alkyl ethers of PEG or PPG, are also suitable for use herein.

Also useful herein as skin conditioning agents are sphingolipids, such as ceramides, sphingosines, phytosphingosines, and the like; and phospholipids, such as lecithin, cephalin, phosphatidylserine, phosphatidylinositol, phosphatidic acid, sphingomyelin, and the like; and mixtures thereof.

Another effective skin conditioning agent having superior barrier properties is a mixture of components which simulate the skin's water-barrier forming lipid complex, particularly vernix (i.e., the substance covering the bodies of fetuses or newborns of human or other mammals). A preferred skin conditioning agent is a simulated vernix, which comprises a mixture of sterols, sterol esters and triglycerides. Other substances occurring naturally in the stratum corneum are also preferred, such as sodium pyrrolidone carboxylic acid, sodium lactate/lactic acid, L-proline, guanidine, pyrrolidone, ceramide, and urea. Other skin conditioning agents derived from natural sources are also suitable for use herein, such as hydrolyzed protein and other collagen-derived proteins, keratin and derivatives, acetamide MEA, and the like.

Vegetable oils and hydrogenated vegetable oils are also useful herein. Non-limiting examples include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, jojoba oil, tea tree oil, avocado oil, olive oil, canola oil, their hydrogenated products such as cocoa butter, shea butter, and mixtures thereof. Some of the fully or partially hydrogenated vegetable oils may be solid or semi-solid (i.e., having a waxy consistency) at ambient temperature such that they are also suitable for use herein as viscosity enhancing agents.

Also useful herein are animal fats and oils such as shark liver oil, cod liver oil, lanolin, their derivatives, and mixtures thereof. In some embodiments, the skin conditioning agent comprises petrolatum and a mixture of lanolin and lanolin derivatives in a ratio ranging from about 1:2 to about 1:5.

Nonlimiting examples of sterols suitable for use herein include cholesterol, ergosterol, sitosterol, cholecalciferol, and other sterols found in phytosterols, soy sterols or tall oil sterols; lanosterols and other sterols found in lanolin and hydrogenated lanolin; and derivatives thereof, such as acetylated lanolin (e.g., ACYLAN® from Croda Inc., Parsippany, N.J.).

Nonlimiting examples of sterol esters suitable for use herein include stearate, palmitate, acetate, lanolate, macadamiate, nonanoate, oleate, butyrate, hydroxystearate, isostearate, sulfate, isostearate carbonate of cholesterol and other sterols. A particularly preferred sterol esters is a mixture of C10–C30 carboxylic acid esters of sterols, which is predominantly a cholesterol/lanosterol mixture (e.g., Super Sterol Ester® from Croda, Inc., Parsippany, N.J.). Super Sterol Ester® is derived from wool wax by a process disclosed in part in U.S. Pat. No. 4,138,416 issued to Koresawa et al., which is incorporated herein by reference. Other nonlimiting examples of sterol esters suitable for use herein include stearate, palmitate, acetate, lanolate, macadamiate, nonanoate, oleate, butyrate, hydroxystearate, isostearate, sulfate, isostearate carbonate of cholesterol and other sterols.

Also useful herein as skin conditioning agents are C7–C40 branched hydrocarbons, such as ISOPAR® isoparaffins (available from Exxon Chemical Company, Houston, Tex.) and PERMETHYL® (available from Presperse Inc., Piscataway, N.J.). Squalane, squalene, and the like are also suitable skin conditioning agents. Squalene, being the partially unsaturated form of squalane, is oxidatively unstable and may require incorporation of anti-oxidants.

Suitable skin conditioning agents also include polysiloxanes having monomeric siloxane units of the following structure:

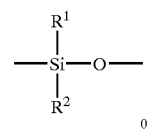

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities. Preferably, the polysiloxane suitable for use as skin conditioning agent herein has a branched, cyclic and/or unsaturated structure in at least one of the R radicals.

Exemplary alkyl radicals are typically C1–C10 alkyls, including methyl, ethyl, propyl, isopropyl, butyl, isobutyl, pentyl, hexyl, octyl, decyl, and the like. Exemplary alkenyl radicals are vinyl, allyl, and the like. Exemplary aryl radicals are phenyl, diphenyl, naphthyl, and the like. Exemplary alkaryl radicals are tolyl, xylyl, ethylphenyl, and the like. Exemplary aryl radicals are benzyl, α-phenylethyl, β-phenylethyl, α-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluoroethyl, fluoroethyl, trifluoroethyl, trifluorotloyl, hexafluoroxylyl, and the like.

In some embodiments, the skin conditioning agent may be a substituted polymethylsiloxane wherein at lease one substituent is a functional group selected form the group consisting of methyl, phenyl, amino, other alkyl, carboxyl, hydroxyl, ether, polyether, aldehyde, ketone, amide, ester, thiol, and mixtures thereof. Particularly preferred for use herein is polydimethylsiloxane.

Viscosity of polysiloxanes useful for the present invention may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves can be effectively deposited upon the absorbent articles by such methods as, for example, emulsifying the polysiloxane in surfactant or providing the polysiloxane in solution with the aid of a solvent, such as hexane, listed for exemplary purposes only.

Particularly suitable for use herein are polysiloxane compounds having long (C12–C60, preferably C30–C50) linear alkyl groups or phenyl groups, including phenyl-functional polymethylsiloxane compounds (e.g., polyphenylmethyl siloxane available as Dow Coming 556 Fluid) and cetyl or stearyl functionalized dimethicones such as Dow 2502 and Dow 2503 polysiloxanes, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Other alkyl polysiloxanes include SF 1318, SF 1642 and SF 1632 (available from General Electric, Corp., Waterford, N.Y.), trimethyl siloxysilicates such as WACKER-BEL-SIL® TSM 803 MQ (available from Wacker Silicones, Adrian, Mich) and MIRASIL® DPDM (available from Rhone-Poulenc, Cranbury, N.J.) are used in some embodiments. Other preferred polysiloxane compounds for use in the present invention are disclosed in U.S. Pat. No. 5,059,282 (Ampulski et al), issued Oct. 22, 1991, which is incorporated herein by reference.

B. Viscosity Enhancing Agents

The compositions of the present invention contain viscosity enhancing agents that thickens, gels, or hardens the composition such that the composition is immobilized or locked at the location (e.g., on the surface or inside the cavity of the delivery vehicle) it is applied. When an absorbent article is used as the delivery vehicle, the viscosity enhancing agent is especially useful in minimizing the migration and loss of the film-forming compositions which, without the viscosity enhancing agents, would have a plastic or fluid consistency at ambient temperature.

The amount of the viscosity enhancing agent in the composition will depend on a variety of factors, including the skin conditioning agents used, especially their viscosity at room temperature and at skin temperature, and their melting points, characteristics of other components in the composition (e.g., skin care ingredients), and like factors. When present, the composition typically comprises from about 15 to about 50 wt % of the viscosity enhancing agent. Preferably, the composition comprises from about 20 to about 45 wt %, most preferably from about 25 to about 40 wt %, of the viscosity enhancing agent.

Exemplary viscosity enhancing agents include organic materials such as natural or synthetic waxes, C12–C60 alcohols, C12–C60 acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays. Other suitable viscosity enhancing agents are disclosed in co-pending U.S. Pat. application Ser. No. 09/563,638, filed by Gatto et al. on May 2, 2000, the disclosure of which is hereby incorporated by reference. Some skin conditioning agents, particularly polyol polyesters, glyceryl esters, polyglyceryl esters and polysiloxanes may have a solid or semi-solid at ambient temperature and are also suitable for use herein as viscosity enhancing agents.

The organic viscosity enhancing agents are preferably miscible with (or solubilized in) the skin conditioning agent. The organic viscosity enhancing agents preferably have a melting point of at least about 35° C., preferably at least about 40° C., so that the viscosity enhancing agents do not have a tendency to migrate or flow at ambient temperature. Their high melting points and miscibility with the skin conditioning agents help thickening and solidifying the composition and immobilize the composition in or on the desired location of the delivery vehicle. Typically, the organic viscosity enhancing agents have a melting point in the range of from about 50° C. to about 150° C.

Suitable viscosity enhancing agents include C12–C60 alcohols, preferably C16–C22 fatty alcohols, most preferably crystalline high melting materials selected from the group consisting of cetyl alcohol, stearyl alcohol, behenyl alcohol, and mixtures thereof. Behenyl alcohol is particularly preferred. When employed, the C16–C22 fatty alcohols comprise from about 1 to about 90 wt %, preferably from about 5 to about 50 wt %, more preferably from about 10 to about 30 wt %, of the total weight percent of the viscosity enhancing agents.

Other suitable viscosity enhancing agents include C12–C60 acids, preferably C16–C22 fatty acids, most preferably selected from the group consisting of palmitic acid, stearic acid, behenic acid, oleic acid, linoleic acid, myristic acid, ricinoleic acid, eurcic acid, lauric acid, isostearic acid, and mixtures thereof. Mixtures of palmitic acid and stearic acid are particularly preferred. The substantially linear structure and high melting point of these viscosity enhancing agents speed up the solidification of the composition and lock it to the location on the delivery vehicle where it is deposited. Other suitable viscosity enhancing agents that may be used herein are alpha-hydroxy fatty acids, including 12-hydroxystearic acid, 12-hydroxylauric acid, 16-hydroxyhexadecanoic acid, and mixtures thereof. Nonlimiting examples of suitable fatty acids are further described in U.S. Pat. No. 5,429,816, issued to Hofrichter et al. on Jul. 4, 1995, and U.S. Pat. No. 5,552,136, issued to Motley on Sep. 3, 1996, disclosure of each is incorporated by reference herein.

Waxes are also suitable for use herein as viscosity enhancing agents. Natural waxes may include, but are not limited to, carnauba, ozokerite, beeswax, candelilla, paraffin, ceresin, esparto, ouricuri, rezowax, and other known mined and mineral waxes. Synthetic waxes may include, but are not limited to, paraffin waxes and microcrystalline waxes. It is particularly advantageous to use these waxes that form microcrystalline structures upon cooling and/or solidifying. Without being bound by theory, it is believed that the formation of microcrystallites may overcome the tendency of the components (especially the immiscible or low molecular weight, mobile components) to separate and "lock" or "freeze" the composition into a substantially homogeneous mixture. Exemplary paraffin waxes are available as SHELLWAX®100, 120, 200, 300, and 400 from Shell Chemical Company, Houston, Tex. and as PARAFFIN® S. P. 434 from Strahl and Pitsch Inc., West Babylon, N.Y. Exemplary microcrystalline waxes include SHELLWAX® 405 from Shell Chemical Company; 180-M, W-445, and W-835 from CK-Witco, Greenwich, Conn.; ULTRAFLEX®, BE SQUARE®175 and FORTEX® from Petrolite, Piscataway, N.J.

Also suitable for use herein as viscosity enhancing agents are block copolymers made from styrene and olefinin monomers. Particularly preferred block copolymers for use herein are polystyrene-ethylene/butylene-polystyrene block copolymers. Such linear block copolymers of styrene-ethylene/butylene-styrene (S-EB-S) are commercially available under the trade designation KRATON® G1600 series, particularly KRATON® G-1652, from Kraton Polymers, Houston, Tex. Also preferred for use herein are polystyrene-ethylene-ethylene/propylene-styrene (S-E-EP-S) block copolymers, wherein the ethylene/propylene block is derived from selective hydrogenation of the unsaturation sites within the polystyrene-isoprene/butadiene-styrene block copolymers. Hydrogenated polystyrene-isoprene/butadiene-styrene (S-IB-S) block copolymers are commercially available under the trade designation SEPTON® 4000 series from Kuraray America, Inc. New York, N.Y.

Other suitable viscosity enhancing agents that may be used herein include polyhydroxy fatty acid esters, polyhydroxy fatty acid amides, and mixtures thereof. Preferred esters and amides will have three or more free hydroxy groups on the polyhydroxy moiety and are typically non-ionic in character. Because of the possible skin sensitivity of those using articles to which the composition is applied, these esters and amides should also be relatively mild and non-irritating to the skin. Suitable polyhydroxy fatty acid esters, polyhydroxy fatty acid amides are disclosed in U.S. Pat. No. 5,643,588, issued to Roe et al. on Jul. 1, 1997, the disclosure of which is hereby incorporated by reference.

The inorganic/organic viscosity enhancing agents generally are particulates in the present composition. In addition to thickening, solidifying and immobilizing the composition, these particulate materials are also useful in suspending immiscible components, such as skin care ingredients or other additives, in the composition. For example, hydrophilic or water-soluble skin care ingredients may be substantially uniformly dispersed in the oleaginous compositions. The resulting uniform dispersion improves the processability of the composition, and provides a more uniform application of the skin care ingredients in or on the delivery vehicle.

Suitable viscosity enhancing agents include treated and untreated fumed silicas. Fumed silicas are particles that do not dissolve in the oleaginous compositions. Rather, the viscosity of the oleaginous composition is raised by a hydrogen bonded network of fumed silica particles. Exemplary untreated fumed silicas are available from Cabot Corp., Tuscola, Ill. under the trade designations M5 and MS-55. Exemplary surface-treated fumed silicas are also available from Cabot Corp., Tuscola, Ill. under the trade designations TS-720 and TS-610.

Suitable viscosity enhancing agents also include organo-clays such as modified hectorite and smectite clays These hectorite and smectite clays are modified with quaternary ammonium compounds to make the surface of the clay particles hydrophobic while maintaining hydrophility on the edges of the clay particle due to exposed hydroxyl groups. These organoclays are insoluble particles dispersed in the oleaginous composition and form a hydrogen-bonded network, which increases the viscosity of the composition. Exemplary hectorite clays are available under the trade designations BENTONE® 27, 38, and SD-3, and exemplary bentonite clays are available under the trade designations BENTONE®34, 52 and SD-1 (all are available from Rheox Hightstown, N.J.).

Other viscosity enhancing agents useful in the present invention include metal ester complexes of aluminum, magnesium, or zinc with stearates, benehates, palmitates or laureates.

C. Film-forming Agents

The compositions of the present invention also include film-forming agents. By incorporating the film-forming agents, the compositions are more easily spread over the skin to form a protective barrier coating. The film-forming agents enhance the adherence of the composition to the skin and render the composition resistance to wash-off or rub-off. Consequently, the skin care ingredients in the composition stay on the skin longer. Film-forming agents are preferably soluble or miscible with oleogenous components in the composition to provide a substantially homogeneous mixture. Thus, suitable film-forming agents are preferably oleophilic and water-resistant. The composition of the present invention typically comprises from about 1 to about 20 wt %, preferably from about 2 to about 15 wt %, more preferably from about 5 to about 12 wt %, of the film-forming agent.

Also useful herein as film-forming agents are polyalkenes include polyethylenes having a molecular weight ranging from about 300 to about 3000 (available as PERFORMALENE® from New Phase Technologies, Piscataway, N.J.); polyisobutylenes (available as VISTANEX® from Exxon Chemical Company, Houston, Tex.); polyisobutenes (available as PRESPERSE® from Amoco, Chicago, Ill.); polydecenes (SILKFLO® TM-366NF and TM-364NF, available from Amoco); and hydrogenated polyisobutenes (PANALANE® L-14E and H-300E, available from Lipo Chemicals, Inc., Paterson, N.J.).

Another suitable oleophilic film-forming agents are copolymers of vinylpyrrolidone (PVP) and long chain alpha olefins, including, but are not limited to, PVP/eicosene copolymers (GANEX® V-220 and V-220F), and tricontanyl PVP copolymers (GANEX® WP-660). All are available from International Specialty Products, Wayne, N.J.

Also suitable for use herein as film-forming agents are GLOSSAMER® L6600, available from International Lubricants Inc., Seattle, Wash. This material is a liquid at room temperature. It is synthesized by the copolymerization of purified vegetable oils from *Brassica Campestris* and *Aleurities Fordi* sources.

Also suitable for use herein as film-forming agents are acrylic copolymers having long (C8–C30) alkyl chains to enhance their oleophilicity, such as acrylate/octylacrylamide copolymers (available as DERMACRYL® 79 and LT from National Starch and Chemical, Bridgewater, N.J.). Other suitable film-forming agents include, but are not limited to, polyethylene glycol derivatives of Beeswax (ESTOL® E04BW-3752, E06BW-3753 and E03BW-3751, available from Unichema, Wilmington, Del.); and fatty acid ester/fatty acid anhydride grafted polyolefins wherein the esters and anhydrides are derived from C12–C22 fatty acid moieties, for example, C30–C38 olefin/isopropyl maleate/maleic anhydride copolymer (PERFORMA® V1608, available from New Phase Technologies, Piscataway, N.J.).

D. Optional Other Components

The film forming compositions of the present invention may comprise other components including, but are not limited to, water, surfactants, skin care ingredients, antioxidants, pH buffering systems, disinfectants, antibacterial agents, antiviral agents, pharmaceutical actives, perfumes, pigments, deodorants, opacifiers, astringents, solvents, preservatives, and the like. Most of these materials are well known in the art as additives for such formulations and can be employed in appropriate amounts in the compositions for use herein. Particular preferred surfactants and skin care ingredients are disclosed in more details below.

Surfactants may be incorporated in the film forming composition of the present invention to solubilize or compatiblize certain film-forming agents or viscosity enhancing agents in the skin conditioning agents. Suitable surfactants typically have hydrophilic lipophilic balance (HLB) values no more than about 7. Particularly suitable surfactants are alkyl ethoxylates such as $C_{12}$–$C_{22}$ fatty alcohol ethoxylates having an average degree of ethoxylation of from about 2 to about 30. These and other suitable surfactants are disclosed in U.S. Pat. No. 5,643,588, issued to Roe et al. on Jul. 1, 1997, the disclosure of which is hereby incorporated by reference.

Safe and effective skin care ingredients may be incorporated in the present composition in the amount ranging from about 0.01 to about 15 wt %, preferably from about 0.1 to about 10 wt %, and more preferably from about 1 to about 7 wt %. Such materials include Category I and Category III actives as defined by the U.S. Food and Drug Administration's (FDA) Tentative Final Monograph on Skin Protectant Drug Products for Over-the-Counter Human Use (21 C.F.R. §347). These monographed materials are known to provide multiple skin benefits, such as skin protection, itch prevention, irritation prevention, via various mechanisms. It will be recognized that several of the monographed actives listed below are "skin conditioning agents" as defined herein. Category I actives presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Category III actives presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like.

Other skin care ingredients suitable for the film-forming compositions of the present invention may include, but are not limited to, vitamins, pH control agents or proton donating agents, protease inhibitors, enzyme inhibitors, chelating agents, anti-microbials, skin soothing agents and the like.

Suitable vitamins include A, $B_3$, $B_5$, niacinamide, panthenol, C and derivatives, $D_3$, E and derivatives, such as E acetate. Suitable skin soothing agents include those materials derived from botanical extracts, marine sources, mineral sources, and the like, such as aloe vera, chamomile, calendula, comfrey, yarrow, witch hazel, sea weed, and oat extracts. Other nonlimiting examples of the skin care ingredients are described in co-pending U.S. application Ser. No. 09/041,509, by McOsker et al. filed on Mar. 12, 1998; U.S. application Ser. No. 09/041,232, by Rourke et al filed on Mar. 12, 1998; U.S. application Ser. No. 091041,266, by Roe et al. and U.S. application Ser. No. 09/041,196, by Underiner et al., both filed on Mar. 12, 1998; Patent Application EP 97/120,699 and EP 97/120,700 both by Palumbo et al. and filed on Nov. 26, 1997; U.S. Pat. No. 5,091,193 issued to Enjolras et al, on Feb. 25, 1992; U.S. Pat. No. 4,556,560 issued to Buckingham on Dec. 3, 1985; U.S. Pat. No. 5,376,655 issued to Imaki et al. on Dec. 27, 1994; U.S. Pat. No. 5,091,193 issued to Enjolras et al. on February 25, 1992; U.S. Pat. No. 3,935,862 issued to Kraskin on Feb. 3, 1976; U.S. Pat. No. 5,409,903 issued to Polak et al. on Apr. 25, 1995; U.S. Pat. No. 4,556,560 issued to Buckingham on Dec. 3, 1985; all are incorporated by reference herein.

Particularly preferred skin care ingredients herein include: zinc oxide, talc, starch, allantoin, aloe vera, chamomile, vitamins, hexamidine and its salts and derivatives, hexamidine diisethionate, and its salts, triacetin, phytic acid, ethylenediamine tetraacetic acid (EDTA), phenylsulfonyl fluorides such as 4-(2-aminoethyl)-benzenesulfonylfluoride hydrochloride, chitosan, and mixtures thereof.

These skin care ingredients may comprise from 0.01 to 10 wt %, preferably from about 0.1% to about 6 wt %, more preferably from about 0.1% to about 4 wt % of the composition.

Oxidation of unsaturations in substances, such as unsaturated hydrocarbons, proteins, lecithin and their derivatives, may lead to rancidity of the composition. Anti-oxidants can be added to minimize or prevent the oxidation process, and enhance the shelf life of the composition. Anti-oxidants useful herein should preferably be mild and non-irritating. Anti-oxidants from natural sources are preferred, such as Vitamin E and derivatives, including tocopherol, tocopherol acetate, mixed tocopherols (available as COVI-OX T-50 or T-70 from Henkel Corp, Ambler, Pa.), and the like. These anti-oxidants are also useful as skin anti-oxidants, which minimizes the wrinkles and dullness of the skin and provides a more youthful looking and firmer textured skin.

A preservative will also be needed to prevent bacterial growth and odors thereof, particularly in compositions having a relatively high water content. Suitable preservatives include propyl paraben, methyl paraben, benzyl alcohol, benzalkonium chloride, tribasic calcium phosphate, BHT, or acids such as citric, tartaric, maleic, lactic, malic, benzoic, salicylic, and the like.

Suitable solvents include propylene glycol, glycerine, cyclomethicone, C2–C6 glycols (particularly, ethylene glycol, propylene glycol and hexylene glycol), diol and multihydroxy based solvents.

III. Delivery Vehicles

The composition of the present invention may be applied to the skin by hand or by delivery vehicles. Exemplary delivery vehicles include web materials or substrates such as tissues, wipes, sponges, cotton balls, pads, non-woven webs, patches, bandages, paper, fabrics, and the like. The delivery vehicles may also be canisters, sticks, or stick casings, aerosol dispensers, roller dispensers, pump sprays, trigger sprays, and the like. Any combination of the above is also suitable for use herein as a delivery vehicle. Nonlimiting examples of some delivery vehicles are described in co-pending U.S. patent application Ser. No. 09/326,149, filed by McOsker et al. on Jun. 4, 1999, U.S. patent application Ser. No. 09/370,396, filed by McOsker et al. on Aug. 6, 1999, and U.S. Pat. No. 5,000,356, issued to Johnson et al. on Mar. 19, 1991; all are incorporated herein by reference.

In one embodiment, the delivery vehicle is a disposable absorbent article having the composition of the present invention disposed on at least a component thereof. The suitable component of an absorbent article preferably has a skin-contacting surface such that when the article is worn, the composition disposed on the absorbent article is placed adjacent to the skin. Suitable components of an absorbent article may also be a secondary layer (which does not have a surface in direct contact with the skin) that will transfer the composition to the skin indirectly. Thus, the component of an absorbent article suitable for such use may be a topsheet, a backsheet, any secondary layer, a leg cuff, a side panel, a waist region, an insertable element inserted into the absorbent article for use during wear of the article, a specialized structure such as a bowel movement "pockets", and the combinations thereof.

In a preferred embodiment, the delivery vehicle is a diaper having the general structure as shown in FIG. 1. FIG. 1 is a plan view of a diaper 20 in a flat-out state with portions of the structure being cut-away to more clearly show the construction of the diaper 20. The portion of the diaper 20 that faces the wearer is oriented towards the viewer. As shown in FIG. 1, the diaper 20 comprises a liquid pervious topsheet 24; a liquid impervious backsheet 26; an absorbent core 28 positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region 36, a second waist region 38 opposed to the waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

Exemplary absorbent articles such as diapers are disclosed in U.S. Pat. No. 3,860,003 issued to Buell on Jan. 14, 1975, U.S. Pat. No. 5,151,092 issued to Buell et al. on Sep. 29, 1992, U.S. Pat. No. 5,221,274 issued to Buell et al. on Jun. 22, 1993, U.S. Pat. No. 5,554,145 issued to Roe et al. on Sep. 10, 1996, U.S. Pat. No. 5,569,234 issued to Buell et al. on Oct. 29, 1996, and U.S. Pat. No. 5,580,411 issued to Nease et al. on Dec. 3, 1996, the disclosure of each of which is incorporated herein by reference.

Exemplary training pants are disclosed in U.S. Pat. No. 5,246,433, issued to Hasse, et al. on Sep. 21, 1993, U.S. Pat. No. 5,569,234, issued to Buell et al. on Oct. 29, 1996, U.S. Pat. No. 6,120,487, issued to Ashton on Sep. 19, 2000, U.S. Pat. No. 6,120,489, issued to Johnson et al. On Sep. 19, 2000, U.S. Pat. No. 4,940,464, issued to Van Gompel et al. on Jul. 10, 1990 and U.S. Pat. No. 5,092,861, issued to Nomura et al. on Mar. 3, 1992, the disclosure of each of these references is incorporated herein by reference.

Exemplary feminine hygiene articles are disclosed in U.S. Pat. No. 4,556,146, issued to Swanson et al. on Dec. 3, 1985, U.S. Pat. No. 4,589,876, issued to Van Tilberg on Apr. 27, 1993, U.S. Pat. No. 4,687,478, issued to Van Tilburg on Aug. 18, 1997, U.S. Pat. No. 4,950,264, issued to Osborn, III on Aug. 21, 1990, U.S. Pat. No. 5,009,653, issued to Osborn, III on Apr. 23, 1991, U.S. Pat. No. 5,267,992, issued to Van Tilburg on Dec. 7, 1993, U.S. Pat. No. 5,389,094, issued to Lavash et al. on Feb. 14, 1995, U.S. Pat. No. 5,413,568, issued to Roach et al. on May 9, 1995, U.S. Pat. No. 5,460,623, issued to Emenaker et al. on Oct. 24, 1995, U.S. Pat. No. 5,489,283, issued Van Tilburg on Feb. 6, 1996, U.S. Pat. No. 5,569,231, issued to Emenaker et al. on Oct. 29, 1996, and U.S. Pat. No. 5,620,430, issued to Bamber on Apr. 15, 1997, the disclosure of each of these references is incorporated by reference herein.

Exemplary incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. Pat. No. 5,304,161 issued Apr. 19, 1994 to Noel, et al., the disclosure of each of these references is incorporated herein.

EXAMPLES

The following examples further describe embodiments within the scope of the present invention. Each film-forming composition is formed by combining and mixing the ingredients at a temperature in the range from about 77° C. to about 120° C. and using technologies known in the art. The examples are given solely for the purpose of illustration and are not to be construed as limitations of the present invention, as many variations thereof are possible without departing form the spirit and scope of the invention.

Examples 1–5

The following are compositions representative of the present invention:

| INGREDIENTS | WEIGHT % |
|---|---|
| EXAMPLE 1 | |
| Petrolatum (PERFECTA ®) | 48.9 |
| Lanolin Oil (VIGILAN ®) | 12.0 |
| Acetylated Lanolin (FANCOL ACEL ®) | 12.0 |
| Behenyl Alcohol/Stearyl Alcohol Mixture (LANETTE ® 22) | 21.0 |
| $C_{30-38}$ olefin/isopropyl maleate/maleic anhydride Copolymer (PERFORMA ® V 1608) | 6.0 |
| Vitamin E Acetate | 0.1 |
| EXAMPLE 2 | |
| Petrolatum (PERFECTA ®) | 52.1 |
| Mineral Oil (HYDROBRITE ®550 PO) | 21.0 |
| Microcrystalline Wax W-835 | 13.0 |
| Stearyl Alcohol CO-1897 | 10.0 |
| Tricontanyl PVP (GANEX ® WP-660) | 3.0 |
| CHAMOMILE PHYTOCONCENTROL ® | 0.9 |
| EXAMPLE 3 | |
| Petrolatum (PERFECTA ®) | 44.4 |
| Isononyl Isonanoate (SALACOS ® 99) | 9.5 |
| $C_{30-45}$ Alkyl Dimethicone SF1642 | 9.5 |
| Microcrystalline Wax W835 | 14.0 |
| Fumed Silica (CAB-O-SIL ® TS-720) | 2.0 |
| Polyethylene (PERFORMALENE ® 400) | 15.0 |
| Acrylates/Ocylacrylamide Copolymer (DERMACRYL ® 79) | 3.0 |
| Dimethicone (DC 200 Fluid) | 1.0 |
| Polyglyceryl-6 polyricinoleate (HEXALYN ® PR-15) | 0.1 |
| Zinc Oxide (USP ®-1) | 1.0 |
| D-Panthenol | 0.5 |
| EXAMPLE 4 | |
| Petrolatum (PERFECTA ®) | 60.0 |
| Behenyl Alcohol/Stearyl Alcohol Mixture (LANETTE ® 22) | 16.0 |
| Microcrystalline Wax W-835 | 10.0 |
| Isononyl Isonanoate (SALACOS ® 99) | 7.0 |
| Copolymerized Vegetable Oils (GLOSSAMER ® L6600) | 5.8 |
| Dimethicone (DC 200 Fluid) | 1.0 |
| Bisabolol (DRAGOSANTOL ®) | 0.1 |
| D&C Green 6 | 0.1 |
| EXAMPLE 5 | |
| Petrolatum (PERFECTA ®) | 28.0 |
| Mineral Oil (HYDROBRITE ® 550 PO) | 24.0 |
| Isononyl Isonanoate (SALACOS ® 99) | 7.0 |
| $C_{30-45}$ Alkyl Dimethicone SF1642 | 6.0 |
| Cetereayl Methicone SF 1632 | 6.0 |
| Ozokerite Wax | 16.0 |
| Polyethylene (PERFORMALENE ® 400) | 3.0 |
| Polyethylene (PERFORMALENE ® 655) | 3.0 |
| PVP/Eicosene Copolymer (GANEX ® V-220) | 2.0 |
| Acrylate/Ocylacrylamide Copolymer (DERMACRYL ® 79) | 3.0 |
| Dimethicone (DC 200 Fluid) | 1.0 |
| D-Panthenol | 1.0 |

Petrolatum and mineral oil are from Witco Corp., Greenwich, Conn. Lanolin oil and acetylated lanolin alcohol are available from Fanning Corp., Chicago, Ill. Stearyl alcohol is available from The Procter & Gamble Company, Cincinnati, Ohio. Behenyl alcohol/stearyl alcohol mixture (LANETTE® 22) is available from Cognis Corp., Cincinnati, Ohio. Dimethicone is available from Dow Corning Corp., Midland, Mich. Methicone derivatives SF 1642 and SF 1632 are available from General Electric Corp., Waterford, N.Y. SALACOS® 99 is available from Nisshin Oil Mills, Ltd., Tokyo, Japan. HEXAGLYN® PR-15 is available from Nikko Chemicals Co. Ltd., Tokyo, Japan. Microcrystalline wax is available from Witco corp., Greenwich, Conn. PERFORMA® 400 and 655 are available from New Phase Technologies, Piscataway, N.J. GANEX® is available from International Specialty Products, Wayne, N.J. DERMACRYL® is available from National Starch & Chemical, Bridgewater, N.J. CRODAMOL® is available from Croda Inc., Parsippany, N.J. Zinc oxide is available from Zinc Corp. of America, Monaca, Pa. GLOSSAMER® L6600 is available from International Lubricants Inc., Seattle, Wash. Vitamin E acetate and D-panthenol available from Roche Vitamins, Inc., Parsippany, N.J. CHAMOMILE PHYTOCONCENTROL® and DRAGOSANTOL® are available from Dragoco, Totowa, N.J. D&C Green is available from Warner Jenkinson Co. Inc., South Plainfield, N.J.

Example 6

Preparation of a Treated Absorbent Article Having A Film-Forming Composition Disposed Thereon A film-forming composition as described above in Example 1 is prepared by combining and mixing the ingredients at about 77° C. (i.e., about 170° F.) and using technology known in the art. Then, the composition is deposited on the topsheet of an absorbent article via a contact slot coater, such as a hot melt adhesive applicator head having multiple slots (Meltex EP11, available from Nordson Corp., Atlanta, Ga.). The composition is placed into a heated tank operating at a temperature of about 77° C. (i.e., about 170° F.). The composition is subsequently applied with a contact applicator onto the topsheet and/or cuffs of a desired article in a striped pattern where the stripes run in the article's longitudinal direction. Specifically, 5 stripes are applied, each stripe measuring about 0.25 inch in width (i.e., the substrate's lateral direction), about 11.7 inches in the longitudinal direction of the substrate, and at an add-on level of about 15.5 mg/in$^2$ (2.4 mg/cm$^2$). The distance between the stripes is about 0.31 inch.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a film-forming composition disposed on at least a skin-contacting surface of the absorbent article, wherein the composition is substantially anhydrous and is solid or semi-solid at room temperature, the composition comprises:
   a. from about 1 to about 80 wt % of a skin conditioning agent selected from the group consisting of petroleum-based emollients; fatty acid esters; polysiloxanes; polyol polyesters; esters or ethers of polyhydroxy alcohols; fatty alcohol esters of polyprotonic acids; animal oils, fats, and their derivatives; vegetable oils, hydrogenated vegetable oils, and their derivatives; branched hydrocarbons; fatty alcohol ethers; free sterols, sterol esters and their derivatives; sphingolipids; phospholipids; and mixtures thereof;
   b. from about 15 to about 50 wt % of a viscosity enhancing agent selected from the group consisting of C12–C60 alcohols, waxes, fumed silicas, and mixtures thereof;
   c. from about 1 to about 20 wt % of a film-forming agent selected from of polyalkenes, PVP/alpha-olefm copolymers, acrylic copolymers, and mixtures thereof; and
   d. optionally, from about 0.01 to about 10 wt % of a skin care ingredient selected from the group consisting of Monographed I actives, Monographed III actives, vitamins, proton donating agents, protease inhibitors, enzyme inhibitors, chelating agents, anti-microbials, skin soothing agents, and mixtures thereof; and
wherein the composition is resistant to water, wash-off, and rub-off.

2. The disposable absorbent article of claim 1, wherein the skin-contacting surface is selected from the group consisting of a topsheet, a cuff, a side panel, a waist region, a secondary layer underlying a topsheet, a bowel movement pocket, an insertable element inserted into the absorbent article for use during wear, and combinations thereof.

3. The disposable absorbent article of claim 1, wherein the skin conditioning agent is a pretroleum-based emollient selected from the group consisting of petrolatum, mineral oil, and mixtures thereof.

4. The disposable absorbent article of claim 1, wherein the viscosity enhancing agent is an organic viscosity enhancing agent having a melting point of at least about 350° C.

5. The disposable absorbent article of claim 1, wherein the viscosity enhancing agent is a wax.

6. The disposable absorbent article of claim 1, wherein the viscosity enhancing agent is an alcohol selected from the group consisting of cetyl alcohol, stearyl alcohol, behenyl alcohol, and mixtures thereof.

* * * * *

UNITED STATES PATENT AND TRADEMARK OFFICE
CERTIFICATE OF CORRECTION

| | | |
|---|---|---|
| PATENT NO. | : 7,005,557 B2 | |
| APPLICATION NO. | : 09/898880 | |
| DATED | : February 28, 2006 | |
| INVENTOR(S) | : Klofta et al. | |

It is certified that error appears in the above-identified patent and that said Letters Patent is hereby corrected as shown below:

Column 7
Line 2, please delete "mon-," and insert --mono,--.
Line 60, please delete "esters" and insert --ester--.
Column 8
Line 54, please delete "lease" and insert --least--.
Line 55, please delete "form" and insert --from--.
Column 9
Line 24, after "Electric", please delete "," (the comma).
Line 36, please delete "thickens" and insert --thicken--; delete "gels" and insert --gel--; and delete "hardens" and insert --harden--.
Lines 52, 54 and 55, please delete "wt %" and insert --wt%--.
Column 10
Lines 22, 23, and 24, please delete "wt %" and insert --wt%--.
Column 11
Line 51, between "clays" and "These", please insert --.--(a period).
Column 12
Lines 14, 15 and 16, please delete "wt %" and insert --wt%--.
Line 19, please delete "include" and insert --including--.
Column 13
Lines 15, 16, and 17, please delete "wt %" and insert --wt%--.
Line 52, please delete "091041,266" and insert --09/041,266--.
Lines 59, 60, and 61, please delete "U.S. Pat. No. 5,091,193 issued to Enjolras et al. on February 25, 1992;".
Lines 63 and 64, please delete "U.S. Pat. No. 4,556,560 issued to Buckingham on Dec. 3, 1985;".
Column 14
Lines 6 and 7, please delete "wt %" and insert --wt%--.
Line 18, please delete "Corp," and insert --Corp.,--
Line 20, please delete "minimizes" and insert --minimize--; and delete "provides" and insert --provide--.
Line 64, please delete "pockets" and insert --"pocket"--.
Column 15
Line 12, between "the" and "waist", please insert --first--.
Column 16
Line 6, please delete "form" and insert --from--.
Column 17
Line 5, please delete "Coming" and insert --Corning--.

UNITED STATES PATENT AND TRADEMARK OFFICE
CERTIFICATE OF CORRECTION

PATENT NO. : 7,005,557 B2
APPLICATION NO. : 09/898880
DATED : February 28, 2006
INVENTOR(S) : Klofta et al.

It is certified that error appears in the above-identified patent and that said Letters Patent is hereby corrected as shown below:

<u>Column 18</u>
Lines 11, 21, 25, and 29, please delete "wt %" and insert --wt%--.
Line 26, after "from", please delete "of"; and please delete "olefm" and insert --olefin--.
Line 45, please delete "pretroleum" and insert --petroleum--.
Line 50, please delete "350°" and insert --35°--.

Signed and Sealed this

Fifth Day of February, 2008

JON W. DUDAS
*Director of the United States Patent and Trademark Office*